US012661146B2

(12) United States Patent　　　　(10) Patent No.:　US 12,661,146 B2
　　Chakfe et al.　　　　　　　　　　(45) Date of Patent:　　　Jun. 23, 2026

(54) DEVICE FOR ANCHORING AN INTRODUCER OF A MEDICAL DEVICE INTO THE HUMAN BODY AND METHOD THEREOF

(71) Applicants: Université de Strasbourg, Strasbourg (FR); Hôpitaux Universitaires de Strasbourg (HUS), Strasbourg (FR)

(72) Inventors: Nabil Chakfe, Hindisheim (FR); Nicole Neumann, Illkirch Graffenstaden (FR)

(73) Assignees: Université de Strasbourg, Strasbourg (FR); Hôpitaux Universitaires de Strasbourg (HUS), Strasbourg (FR)

( * ) Notice: Subject to any disclaimer, the term of this patent is extended or adjusted under 35 U.S.C. 154(b) by 609 days.

(21) Appl. No.: 18/246,622

(22) PCT Filed: Sep. 29, 2021

(86) PCT No.: PCT/EP2021/076768
　§ 371 (c)(1),
　(2) Date: Mar. 24, 2023

(87) PCT Pub. No.: WO2022/069529
　PCT Pub. Date: Apr. 7, 2022

(65) Prior Publication Data
　US 2023/0363791 A1　　Nov. 16, 2023

(30) Foreign Application Priority Data
　Sep. 29, 2020　(EP) .................................... 20306113

(51) Int. Cl.
　*A61B 17/34*　　　(2006.01)
(52) U.S. Cl.
　CPC .......... *A61B 17/3423* (2013.01); *A61B 17/34* (2013.01); *A61B 2017/3484* (2013.01)

(58) Field of Classification Search
　CPC ................ A61B 17/3423; A61B 17/34; A61B 2017/3484; A61B 90/50;
　　　　　　　　　　　(Continued)

(56) References Cited

U.S. PATENT DOCUMENTS 6,113,536 A　　9/2000　Aboul-Hosn et al.
6,572,588 B1 *　6/2003　Bierman ............... A61M 25/02
　　　　　　　　　　　　　　　　　　604/174

(Continued)

FOREIGN PATENT DOCUMENTS

EP　　　2626101 A1　　8/2013
EP　　　2889006 A1　　7/2015

(Continued)

OTHER PUBLICATIONS

European Search Report issued for European Patent Application No. 20 30 6113, dated Mar. 22, 2021 in 9 pages.

(Continued)

*Primary Examiner* — Theodore J Stigell
(74) *Attorney, Agent, or Firm* — Knobbe, Martens, Olson & Bear, LLP

(57)　　　　　　ABSTRACT

This anchoring device (10) comprises:
　a support (14) to be held on the patient;
　a connecting assembly (18) mounted on the support (14);
　an introducer (12) receiving a clip (16) attached to the connecting assembly (18), the clip (16) defining a central passage (60) extending along a longitudinal axis (B) and a longitudinal opening (62) for inserting the introducer (12); and
　a holding system (20) for holding the introducer (12) in position in the dip (16).
The holding system (20) includes at least one reversible locking pad (88) for immobilizing the introducer (12), the (Continued)

holding system (20) being able to change from a released configuration to a configuration in which the introducer (12) is locked in position.

17 Claims, 16 Drawing Sheets

(58) Field of Classification Search
CPC ..... A61B 2017/00477; A61B 17/0206; A61M 25/02; A61M 2025/024; A61M 2025/0293; A61M 2025/028
See application file for complete search history.

(56)                   References Cited

U.S. PATENT DOCUMENTS

| | | | | |
|---|---|---|---|---|
| 7,201,747 | B2 * | 4/2007 | Edoga | A61B 90/50 606/1 |
| 2006/0025723 | A1 * | 2/2006 | Ballarini | A61M 25/02 606/232 |
| 2009/0143742 | A1 | 6/2009 | Bracken et al. | |
| 2009/0247859 | A1 | 10/2009 | Daum et al. | |
| 2015/0217087 | A1 | 8/2015 | Lichtenstein et al. | |

FOREIGN PATENT DOCUMENTS

| | | |
|---|---|---|
| JP | 2003-526483 | 9/2003 |
| JP | 2005-312615 | 11/2005 |
| JP | 2009-533085 | 9/2009 |
| JP | 2013-176534 | 9/2013 |
| JP | 2015-503995 | 2/2015 |
| JP | 2015-163191 | 9/2015 |
| WO | 01/68180 A1 | 9/2001 |
| WO | 2004/037065 A2 | 5/2004 |
| WO | 2005/081882 A2 | 9/2005 |
| WO | 2005/105194 A1 | 11/2005 |
| WO | 2007/028007 A2 | 3/2007 |
| WO | 2007/117655 A2 | 10/2007 |
| WO | 2013/109835 A1 | 7/2013 |
| WO | 2020/078601 A1 | 4/2020 |

OTHER PUBLICATIONS

International Search Report issued for International Patent Application No. PCT/EP2021/076768, dated Dec. 21, 2021 in 9 pages.

* cited by examiner

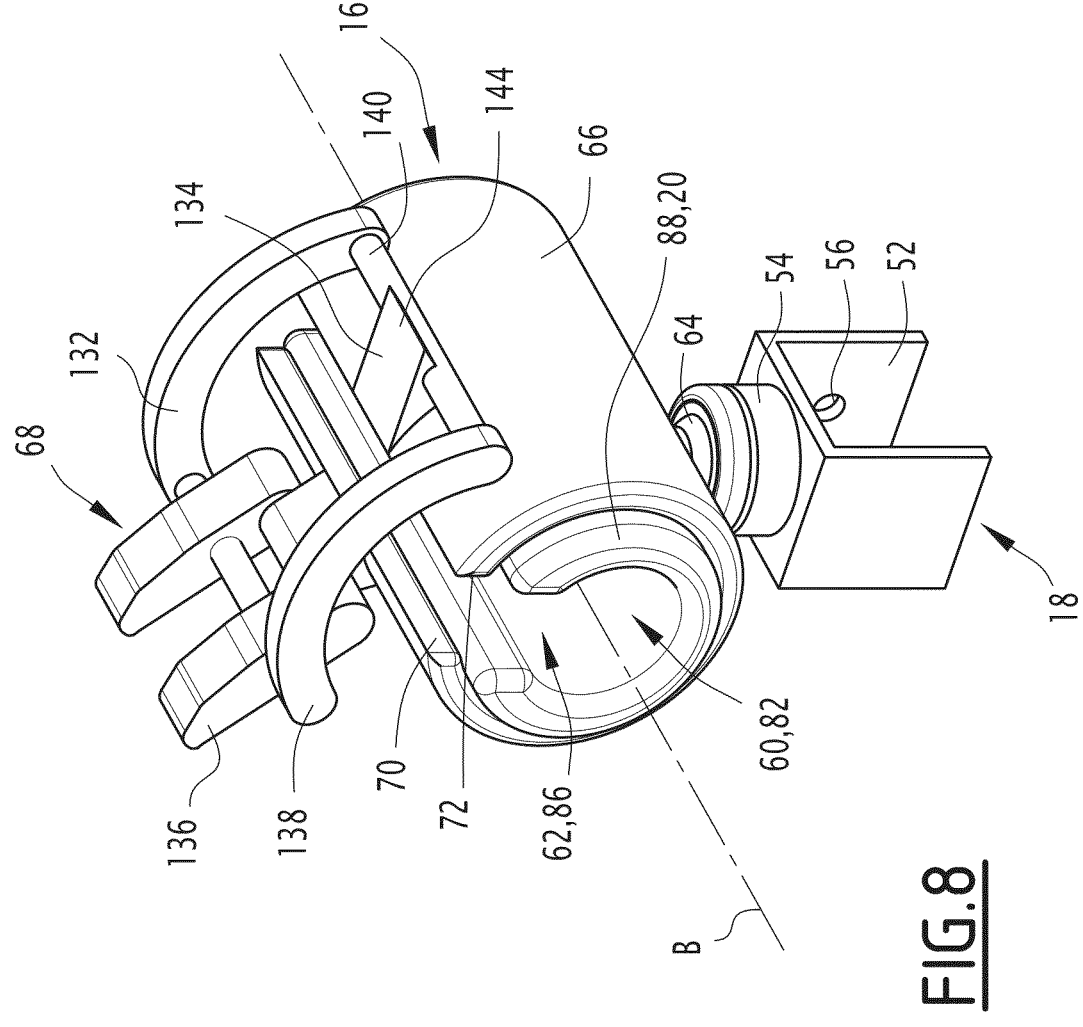
_FIG.8_

DEVICE FOR ANCHORING AN INTRODUCER OF A MEDICAL DEVICE INTO THE HUMAN BODY AND METHOD THEREOF

CROSS-REFERENCE TO RELATED APPLICATIONS

This application is the U.S. National Phase under 35. U.S.C. § 371 of International Application PCT/EP2021/076768, filed Sep. 29, 2021, which claims priority to European Patent Application No. 20306113.0, filed Sep. 29, 2020. The disclosures of the above-described applications are hereby incorporated by reference in their entirety.

FIELD OF THE INVENTION

The present invention relates to a device for anchoring an introducer of a medical device into the human body, comprising:
- a support intended to be held on the patient or relative to the patient;
- a connecting assembly mounted on the support;
- a receiving clip of the introducer, attached to the connecting assembly for mounting on the support, the clip defining a central passage extending along a longitudinal axis and a longitudinal opening for insertion of the introducer into the central passage; and
- a system for holding the introducer in position in the clip.

BACKGROUND OF THE INVENTION

The medical device to be introduced into the human body is, for example, an implant formed by a stent or an endovalve, and an implant delivery tool.

Stents are used, for example, to repair and support the wall of the vessel when it is partially obstructed, or to bridge an aneurysm. Endovalves are used to replace a diseased or defective native valve.

For this purpose, the treatment device carrying the implant is preferably introduced by endoluminal route, in order to avoid surgically opening the thorax of the patient and thus minimizing the operative risks, especially for elderly or weak patients.

In the case where the treatment device is to be conducted to its implantation site through a blood vessel such as the aorta, it is known to be introduced into the bloodstream through an introducer vessel such as the femoral artery, by making an incision in the groin of the patient.

Other introducer vessels such as the carotid artery, the arteries and veins of the upper limbs, or the jugular vein are also used depending on the final implantation site.

An introducer is then required to guide the treatment device from outside the body through the introducer vessel to another blood vessel of larger diameter. According to the treatment device to be introduced, the introducer may have a diameter ranging, for example, from 4 F to 26 F (that is, from 1.3 mm to 8.7 mm).

The introducer has a sealing valve that prevents blood from flowing back out of the patient under pressure by a seal around the treatment device.

During the process of introducing the treatment device through the introducer, there is always a risk that the introducer may move outside the introducing blood vessel. This risk can occur when a device is removed from inside the introducer, such as a stent or catheter, for example, or when the pressure of the pulsed blood flow in the introducer is too high.

This movement of the introducer outside the vessel can lead to the complete expulsion of the introducer and cause the patient to bleed through the puncture site.

In addition, movement of the introducer outside of the vessel may cause the introducer to recoil, leading to an improper positioning of the medical device in the patient.

In order to minimize the risk to the patient, it is therefore necessary to anchor the introducer to avoid movement of the introducer.

Usually, it is known to use an operator in order to manually hold the introducer in a desired position throughout the surgical procedure. However, the surgical procedure may last several hours and there is a risk that the operator may move due to fatigue. In addition, throughout the procedure, radiographic images are taken to verify the positioning of the medical device in the patient. The operator holding the introducer remains in close proximity to the source of radiation emission from the X-ray equipment, which is harmful to the operator.

It is also known to anchor the introducer to the patient with stitches. However, this solution does not allow the position of the introducer to be adapted during the procedure. In addition, this solution requires additional sutures to be placed on the patient.

In order to avoid movement of the introducer, it is also known, for example from WO 2005 081882 A2, to stitch the introducer to a patch glued to the skin of the patient. However, this solution does not allow the position of the introducer to be adapted during the procedure without having to change the patch and move the entire introducer, which creates additional risks for the patient.

SUMMARY OF THE INVENTION

One aim of the invention is to provide a system for anchoring the introducer capable of holding, in a reliable manner, the introducer in a desired anchored position and allowing the adaptation of this position during the surgical procedure, without creating additional risk for the patient.

To this end, the invention has as its object a device for anchoring an introducer of a medical device in the human body, characterized in that the anchoring system includes at least one reversible locking pad for the introducer, the anchoring system being able to change from a released configuration for the positioning, the displacement and the removal of the introducer in the central passage to a configuration for locking the introducer in position in the central passage.

The anchoring device according to the invention may comprise one e of the following features, taken alone or in any technically feasible combination:
- The locking pad includes a sleeve split along a generatrix.
- The locking pad is formed of a block of deformable material, or a bag containing deformable material.
- The holding system comprises an inflation system for the pad controlling the inflation and deflation of the pad.
- The connecting assembly between the clip and the support includes a ball and a ball joint receiving the ball.
- The clip includes a bertha receiving clip being mounted on the support bar by the connecting assembly.
- The receiving clip is slidably mounted along the bar of the support.
- The bar is extendable and the length of the bar is adjustable.

The support includes at least one additional piece attached to the bar to increase the height of the support.

The support includes a spacer.

The support includes a patch.

The receiving clip includes a sleeve deformable between an open position and a closed position.

The receiving clip includes a mechanism for clamping and/or unclamping the deformable sleeve.

The clamping mechanism of the deformable sleeve comprises a notch system, a toggle system or a clamp system.

It comprises a guide fixing system remote from the receiving clip and the support, and advantageously a flexible link connecting the guide fixing system to the support or the receiving clip.

The guide fixing system comprises a holding block attached to a patch defining a slot for receiving the guide.

The invention also has as its object a method for anchoring an introducer of the medical device, implemented outside the human body, comprising the following steps:

providing an anchoring device including a support previously fixed to the patient and a clip for receiving the introducer mounted on the support, the clip defining a central passage extending along a longitudinal axis and a longitudinal opening for inserting the introducer into the central passage, the anchoring device including a system for holding the introducer in position in the clip, the holding system including at least one reversible locking pad for the introducer positioning of the introducer in the central passage through the longitudinal opening, and reversibly shifting the locking pad from a released configuration during the placement of the introducer in the central passage to a configuration of locking the introducer in position in the central passage.

BRIEF DESCRIPTION OF THE DRAWINGS

The invention will be better understood from the following description, given only by way of example, and made with reference to the attached drawings, in which:

FIG. 8 is a perspective view of the receiving clip, the connecting assembly and a holding system of a fifth anchoring device according to the invention.

DETAILED DESCRIPTION OF THE PREFERRED EMBODIMENTS

Figure 1:
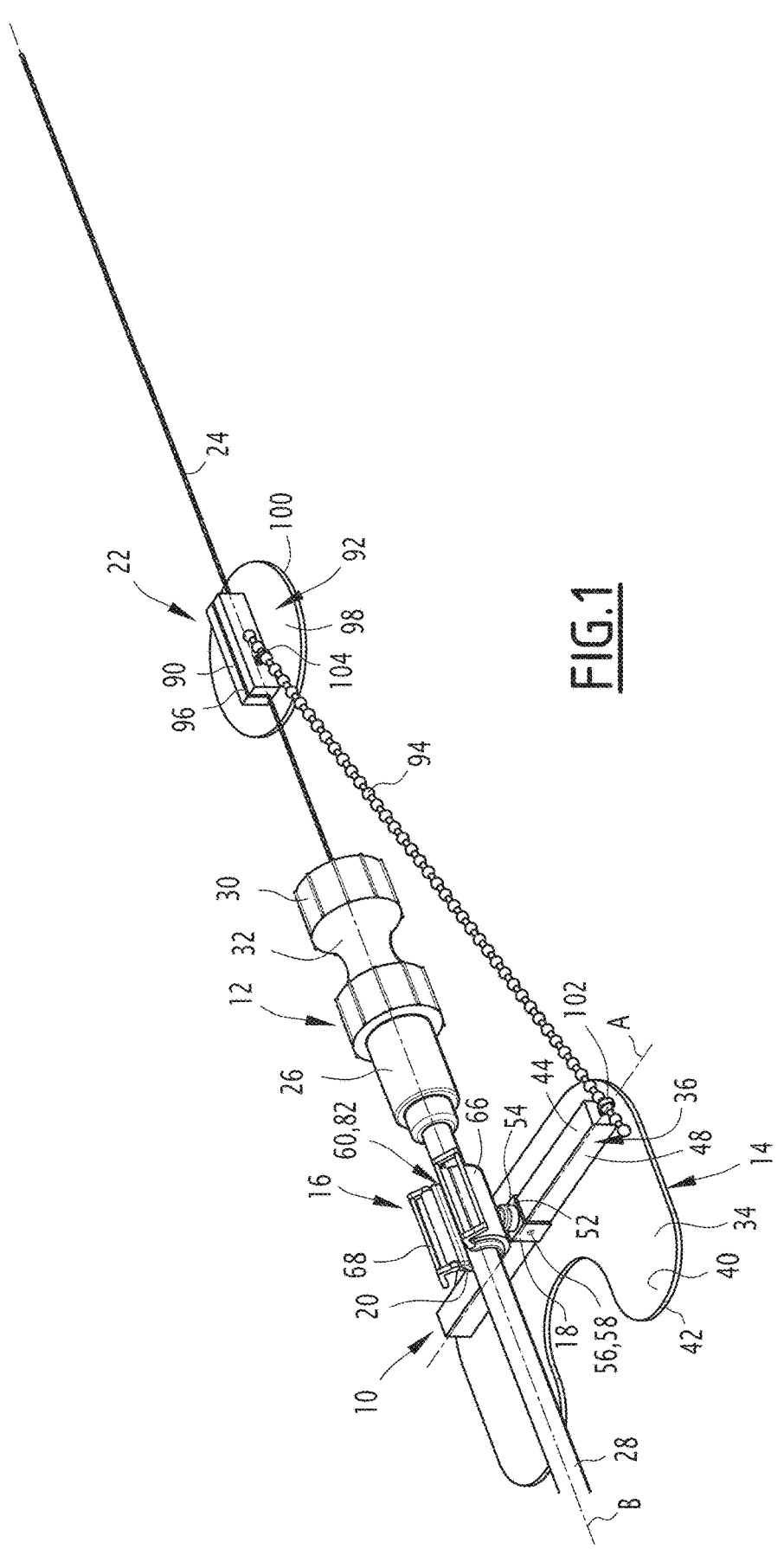
FIG. 1 is a perspective view of a first device for anchoring an introducer of a medical device in the human body.

FIG. 1 illustrates an anchoring device 10 for an introducer 12 of the medical device into the human body.

As seen in FIG. 1, the anchoring device 10 comprises a support 14, a clip 16 for receiving the introducer 12, a connecting assembly 18 connecting the support 14 to the receiving clip 16, and a releasable holding system for holding 20 the introducer 12 in position within the clip 16. Advantageously, the anchoring device 10 includes a system for fixing 22 a surgical guide 24.

By "releasable", it is meant that the holding system 20 is capable of moving from a locking configuration of the introducer 12, in which it firmly holds the introducer 12 in position, to a released configuration in which it allows the introducer 12 to move at least in translation along an axis.

The introducer 12 comprises a hollow introducer tip 26 and a substantially rigid tube 28 for guiding the medical device into the introducer vessel.

The tip 26 comprises a rigid tubular handling body 30 and a sealing valve 32 arranged in the body 30. The valve 32 is able to be opened to introduce the surgical guide 24 into the introducer 12 and then the medical device mounted on the surgical guide 24. It is able to be closed to seal around the guide 24.

The surgical guide 24, intended to navigate within the blood vessels, has here been introduced according to the generatrix of the tube 28 from a proximal point of the tip 26 located outside the human body to a distal point of the tip 26 located inside the human body. The surgical guide 24 is made of a small diameter wire, for example between 0.1 mm and 3 mm.

As illustrated in FIG. 1, the support 14 comprises an adhesive patch 34 and a bar 36 fixed transversely to the patch 34. The support 14 is intended to be fixed to the patient close to the incision in order to define a fixed point on the body of the patient throughout the surgical procedure.

The adhesive patch 34 is a flat horseshoe-shaped adhesive element. The patch 34 defines a first non-adhesive upper surface 40 and a second adhesive lower surface 42 suitable for adhering to the skin of the patient.

Figure 3:
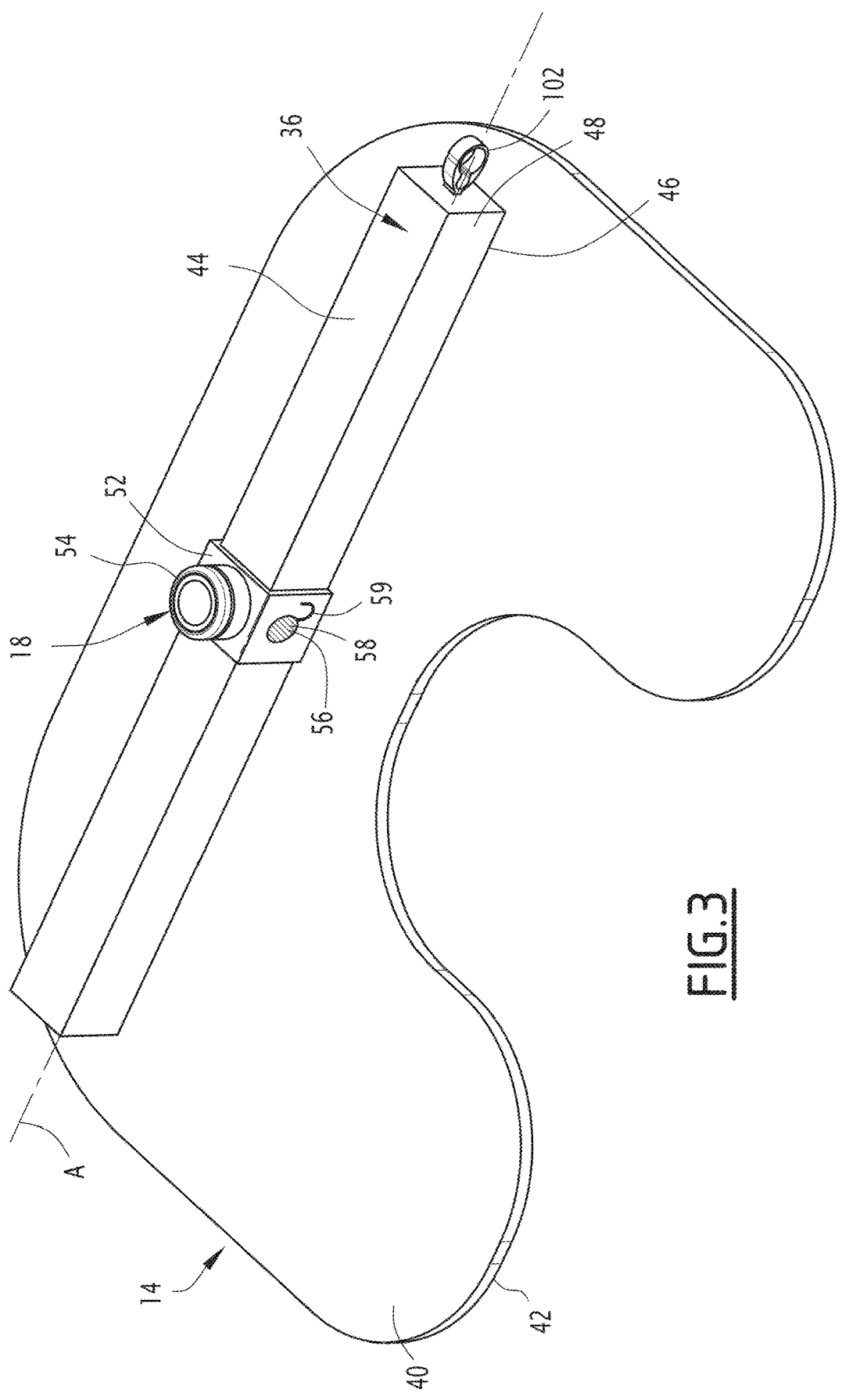
FIG. 3 is a perspective view of the support and connecting assembly of the anchoring device of FIG. 1.

As is shown in FIG. 3, the bar 36 is a straight piece of rectangular cross-section extending along a longitudinal axis A. The bar 36 defines an upper face 44, a lower face 46, and two side faces 48. The lower face 46 of the bar 36 is fixed to the top surface 40 of the patch 34.

The bar 36 is preferably a single-use metal or plastic bar.

The connecting assembly 18 comprises a clamp 52 connected to the bar 36 and a ball joint 54 connected to the clip 16.

The clamp 52 is a U-shaped jumper capable of being fixed to the bar 36. The clamp 52 is mounted on the bar 36 and is movable in translation according to the longitudinal axis A along the bar 36.

The clamp 52 also comprises a threaded hole 56 on one of the side faces thereof capable of receiving a fastening screw 58 or other fastening system.

Tightening the fastening screw 58 in the threaded hole 56 fixes the position of the clamp 52 along the bar 36.

Advantageously, the fastening screw 58 is connected to the clamp 52 by means of a threaded connection 59, for example made of plastic, so that it is not lost in the event of detachment.

Figure 2:
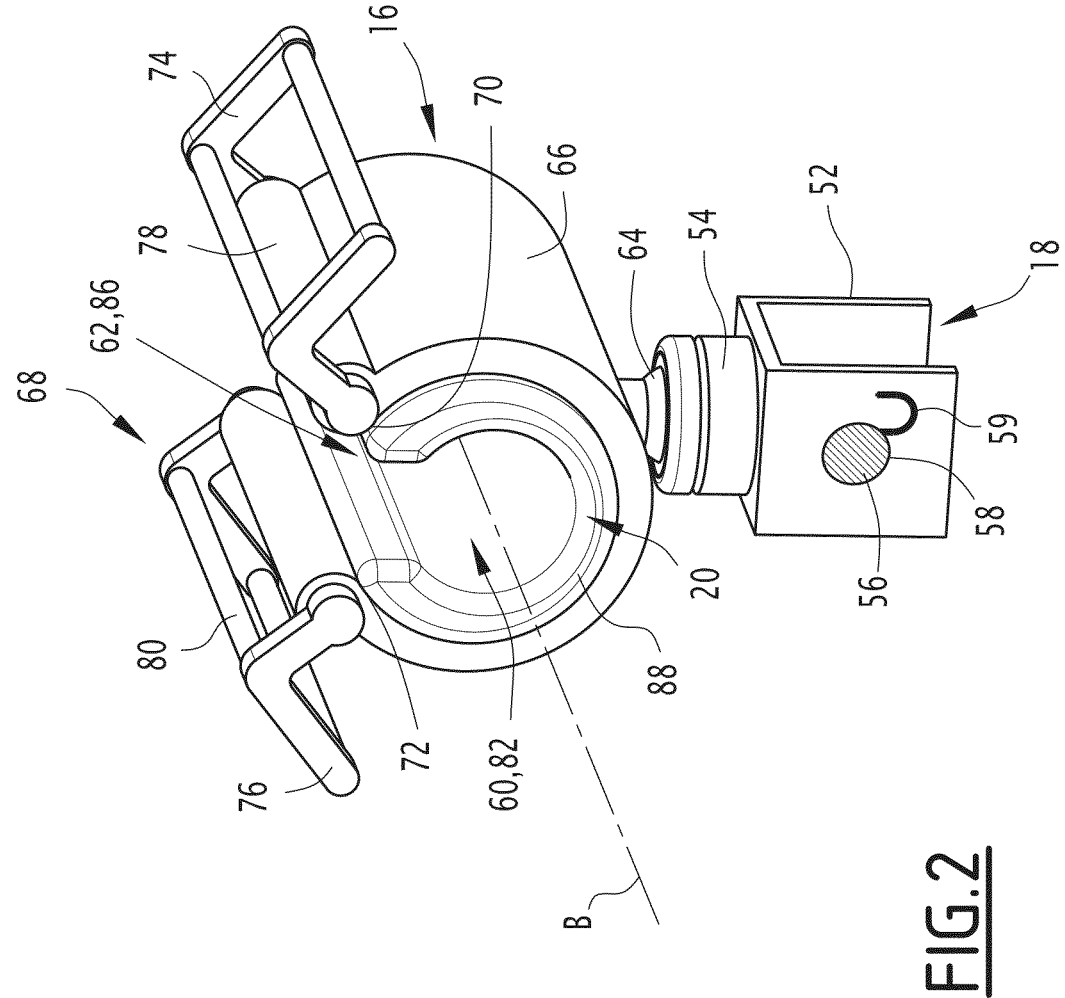
FIG. 2 is a perspective view of the receiving clip, connecting assembly and the holding system of the anchoring device of FIG. 1.

As shown in FIG. 2, the receiving clip 16 defines a central passage 60 extending along a longitudinal axis B and a longitudinal opening 62 for insertion of the introducer 12 into the central passage 60, in the form of a longitudinal slot that opens at its longitudinal ends.

In FIG. 1, the longitudinal axis A of the bar 36 and the longitudinal axis B of the central passage 60 are substantially perpendicular.

The receiving clip 16 comprises a ball 64 received in the connecting assembly 18, a deformable sleeve 66, and a mechanism for releasing 68 the deformable sleeve 66.

The ball 64 is fixed in the ball joint 54 of the connecting assembly 18, thus connecting the clip 16 and the support 14 in a ball-and-socket connection. This ball-and-socket connection provides the ability to orient the clip 16, and therefore the introducer 12, relative to the support 14 fixed to the body of the patient.

The sleeve 66 extends around the central passage 60 and defines a first longitudinal edge 70 and a second longitudinal edge 72 on either side of the longitudinal opening 62. The sleeve 66 is deformable between an open position and a closed position.

In the closed position, the first edge 70 and the second edge 72 of the sleeve 66 are adjacent to and/or in contact with each other causing the longitudinal opening 62 to narrow and therefore making it impossible to insert the introducer 12 into the central passage 60 or to remove the introducer 12 from the central passage 60. In this example, the closed position is the rest position.

In the open position, the first edge 70 and the second edge 72 of the sleeve 66 are away from each other, causing the longitudinal opening 62 to open and therefore making it possible to insert and move the introducer 12 into the central passage 60 or to withdraw the introducer 12 from the central passage 60 through the longitudinal opening 62.

The release mechanism 68 is operable by a practitioner to move the sleeve 66 from the closed position to the open position.

In this example, the release mechanism 68 comprises a first jaw 74 rotatably mounted on the first edge 70 of the sleeve 66 and a second jaw 76 rotatably mounted on the second edge 72 of the sleeve 66.

The two jaws 74, 76 are hinged in rotation relative to the sleeve 66 about the axes parallel to the B axis. When the jaws 74, 76 press against each other, they move the first edge 72 away from the second edge 74 and allow the holding system 20 to be opened to release the introducer 12, as described below.

The holding system 20 for holding the introducer 12 in the clip 16 is fixedly mounted within the sleeve 66 of the receiving clip 16, and is applied to an interior surface of the sleeve 66. It extends into the central passage 60.

The holding system 20 defines a central passage 82 extending along the longitudinal axis B of the central passage 60 and of smaller diameter than the central passage 60 of the clip 16. The holding system 20 also defines a longitudinal opening 86 for insertion of the introducer 12 into the central passage 82 in continuity with the longitudinal opening 62 of the clip 16.

In this example, the holding system 20 comprises a locking pad 88 that presents a cylindrical sleeve shape split along a generatrix.

The locking pad 88 is able to receive the introducer 12, to clamp the introducer 12 in the central passage 82 and hold it in position. It is able to deform so as to partially release the introducer 12, particularly in translation along the axis of the central passage 82.

The holding system 20 thus presents a locked configuration in which the locking pad 88 is compressed between the introducer 12 and the inside of the sleeve 66 and a released configuration, in which the introducer 12 is movable at least in translation in the central passage 82.

Advantageously, the surface texture of the locking pad 88 is rough to prevent the introducer 12 from slipping in the central passage 82 and to combat the hydrophilic treatment of the introducers that is typically associated with allowing the best glide in the arteries.

The locking pad 88 is, for example, made in one piece from an elastomeric material such as silicone, rubber, PVC or is made with a pouch, for example in plastic, containing a deformable material, for example water, oil, gelatin or liquid silicone.

As is shown in FIG. 1, the fixation system 22 for the guide 24 comprises a holding block 90 fixed to an adhesive patch 92 and a flexible link 94 for connection to the support 14.

The holding block 90 defines a slot 96 for receiving the guide 24. The slot 96 has a diameter between 0.1 mm and 3 mm according to the diameter of the corresponding guide 24.

Advantageously, the holding block 90 is made of foam.

The adhesive patch 92 is a flat adhesive element, here of circular shape, defining a non-adhesive upper surface 98 and an adhesive lower surface 100. The holding block 90 is fixed to the upper surface 98 of the adhesive patch 92 by gluing, for example. The lower surface 100 of the adhesive patch 92 is glued to the patient.

The fixation system 22 is fixed to the patient, displaced relative to the support 14, so that the slot 96 for receiving the guide 24 extends substantially along the longitudinal axis B of the receiving clip 16.

The flexible link 94 is advantageously a ball collar fixed at one end to a ring 102 on the bar 36 and at another end to a ring 104 on the holding block 96.

A method of anchoring a medical device introducer 12 in the previously described anchoring device 10 will now be described.

With reference to FIG. 1, the surgical guide 24 is first inserted into the patient to its desired position.

Then, the introducer 12 is positioned by engaging it over the surgical guide 24. The tube 28 is partially inserted into the patient, with the tip 26 remaining outside the patient.

The portion of the surgical guide 24 protruding from the introducer 12 is then inserted into the slot 96 of the holding block 90 thus defining the desired centering axis of the introducer 12.

The support 14 on which the receiving clip 16 is mounted, by means of the connecting assembly 18, is then fixed to the patient by gluing the adhesive lower surface 42 of the patch 34 to a surface of the skin of the patient close to the insertion incision without interfering with the practitioners working space.

The introducer 12 is then inserted into the central passage 82 through the longitudinal openings 62, 86. During passage through the openings 62, 86, the introducer 12 pushes the first edge 70 away from the second edge 72 passing the sleeve 66 into an open position and the pad 88 in a released configuration. When the introducer 12 reaches the passage 60, the sleeve 66 spontaneously returns to its closed position and the pad 88 moves to its locking configuration in which it clamps the introducer 12.

The receiving clip 16 is then moved in translation according to the longitudinal axis A along the bar 36 and oriented by means of the ball joint 64 connected to the connecting assembly 18, so that the longitudinal axis B of the receiving clip 16 coincides with the desired centering axis of the introducer 12.

The adhesive lower surface 100 of the patch 92 is then glued to the skin of the patient in such a way that the flexible link 94 attached on one side to the support 14 and on the other side to the holding block 90 is taut and the receiving slot 96 of the guide 24 extends according to a direction parallel to the longitudinal axis B of the central passage 60.

In this configuration, the locking pad 88 is hi a locked configuration. The locking pad 88 is compressed between the introducer 12 and the inside of the sleeve 66 and thereby holds the introducer 12 in position in the central passage 60 of the clip 16.

The introducer 12 is now fixed in the desired position. The placement of the medical device into the introducer 12 is then performed.

During the procedure, it is possible, if necessary, to adjust the position of the introducer 12 in the central passage 60 while remaining centered relative to the surgical guide 24.

The practitioner presses the two jaws 74, 76 together. The sleeve 66 is thus deformed to move the first edge 70 away from the second edge 72 and into the open position. The locking pad 88 is thus no longer compressed between the introducer 12 and the inside of the sleeve 66. The locking pad 88 is in a released configuration. The introducer 12 can thus be moved into the central passage 60. Upon release of both jaws 74, 76, the sleeve 66 returns to its closed position and the locking pad 88 is again compressed between the introducer 12 and the inside of the sleeve 66 thereby the introducer 12 in a new position.

When placement is complete, the introducer 12 is removed from the clip 16 and the body of the patient. The adhesive patches 34, 92 are then peeled away from the skin of the patient.

The anchoring device 10 according to the invention thus holds the introducer 12 in a desired fixed position, while minimizing risk to the patient and medical personnel.

Furthermore, the holding position of the introducer 12 in the anchoring device 10 is easily adaptable during the surgical procedure, without creating additional risk to the patient, while remaining centered on the centering axis defined by the surgical guide 24.

The device 10 according to the invention is furthermore very versatile since the anchoring device 10 can be used for different diameters of the introducer 12.

Due to the use of adhesive patches 34, 92, the method of anchoring of an introducer 12 leaves only minimal and temporary traces on the body of the patient, unlike stitches for example.

In one alternative, the anchoring device 10 includes a plurality of fixation systems 22 of the surgical guide 24, in order to secure the guide 24 in multiple points.

Figure 4:
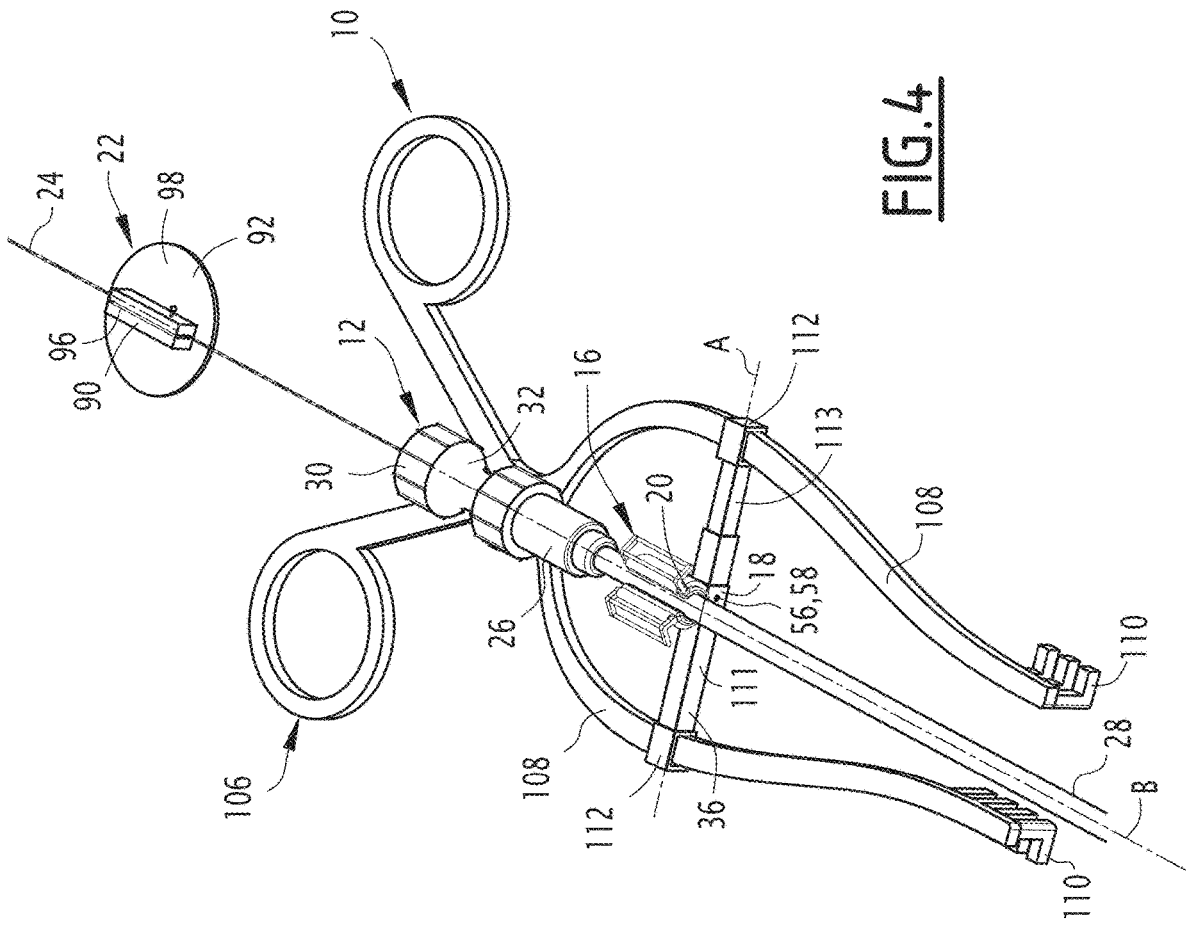
FIG. 4 is a perspective view of a second anchoring device according to the invention.

In one alternative shown in FIG. 4, the support 14 includes a retractor 106. The bar 36 is attached to the retractor 106 instead of being glued to the patch 34.

The retractor 106 includes two opposing legs 108 each for spreading one of the walls of the insertion incision on the body of the patient. Each leg 108 includes a retractor paddle 110 intended to be positioned pressing against one of the edges of the incision.

Figure 5:
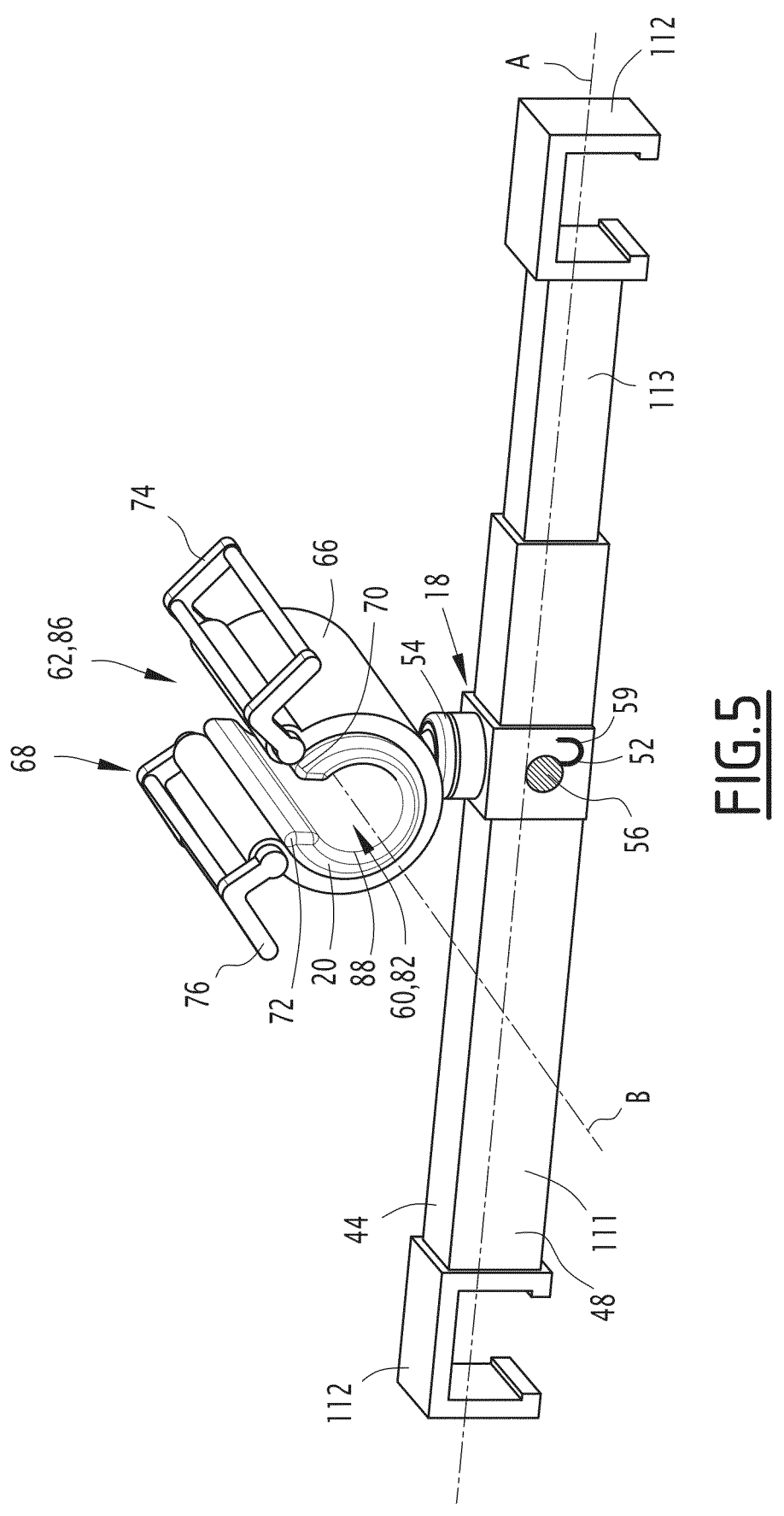
FIG. 5 is a perspective view of the support bar, the receiving clip, the connecting assembly and the holding system of the anchoring device of FIG. 4.

As is shown in FIG. 5, the bar 36 includes a hook 112 at each end capable of being attached to the legs 108 of the retractor 106.

The bar 36 is expandable and the length of the bar 36 is adjustable.

Advantageously, the bar 36 comprises two parts 111, 113 mounted telescopically one inside the other. The length of the bar 36 is thus adjustable, allowing the size of the bar 36 to be adapted to the spacing of the legs 108 of the retractor 106.

In the embodiment with a retractor 106, the anchoring method differs from that of the previous embodiment only for the step of fixing the support 14 to the body of the patient.

Indeed, after spreading the legs 108, each of the retractor paddles 110 is fixed against one of the edges of the incision. The retractor 106 thus allows to define a fixed position on the body of the patient.

The length of the bar 36 is then adjusted according to the spacing of the legs 108 of the retractor 106 by moving the two parts 111, 113 relative to each other. The hooks 112 are then clipped onto the legs 108 of the retractor 106. The bar 36 is thus fixed to the retractor 106 defining the support 14.

Advantageously, the bar 36 is selected to be metallic when a surgical femoral retractor is placed to maintain the previously open route.

In one alternative, the selected retractor 106 is a single-use retractor with a bar 36 already mounted between the two legs 108 of the retractor 106. The single-use retractor thus defines the support 14 on its own.

Figure 6:
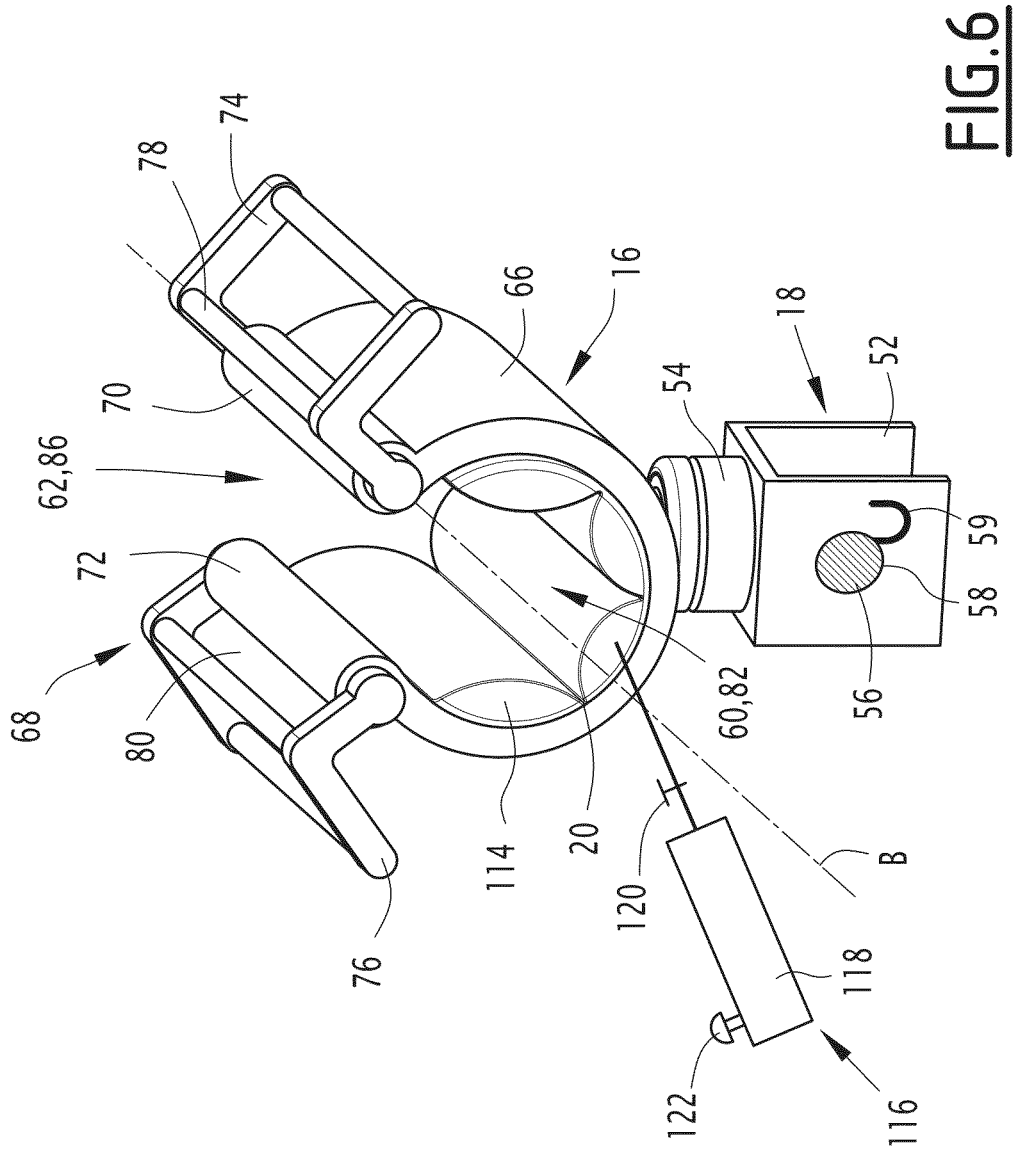
FIG. 6 is a perspective view of the receiving clip, the connecting assembly and a holding system of a third anchoring device according to the invention.

According to another embodiment shown in FIG. 6, the locking pad 88 of the holding system 20 comprises at least one balloon 114 capable of being inflated by the injection of fluid. In FIG. 6, four balloons 114 are shown.

Advantageously, the outer texture of the balloons 114 is rough to prevent slipping The holding system 20 comprises an inflation system 116 for the balloons 114 comprising, for example, a syringe 118 suitable for injecting fluid into the balloons 114 through a valve 120.

Advantageously, the fluid injected into the balloons 114 is water, oil, gelatin or liquid silicone.

The balloons 114 have a compression behavior identical to the pad described above.

The inflation system 116 is controlled by a pressure button 122. Pressing the button 122 allows the valve 120 to open and injects liquid from the pump 118 into the balloons 114, causing the balloons 114 to inflate.

In one alternative (not shown), the mechanism 68 is a clamping mechanism for the sleeve 66. The sleeve 66 is not held at rest in the closed position.

The first jaw 74 presents a notch, and the second jaw 76 includes a stop suitable for engaging the notch.

In order to move the sleeve 66 into the closed position, the practitioner pivots the first jaw 74 upward and simultaneously pivots the second jaw 76 upward. He brings the two jaws 74, 76 into contact. The stop of the second jaw 76 thus engages the notch of the first jaw 74, ensuring that the sleeve 66 moves from the open position to the closed position.

Figure 7:
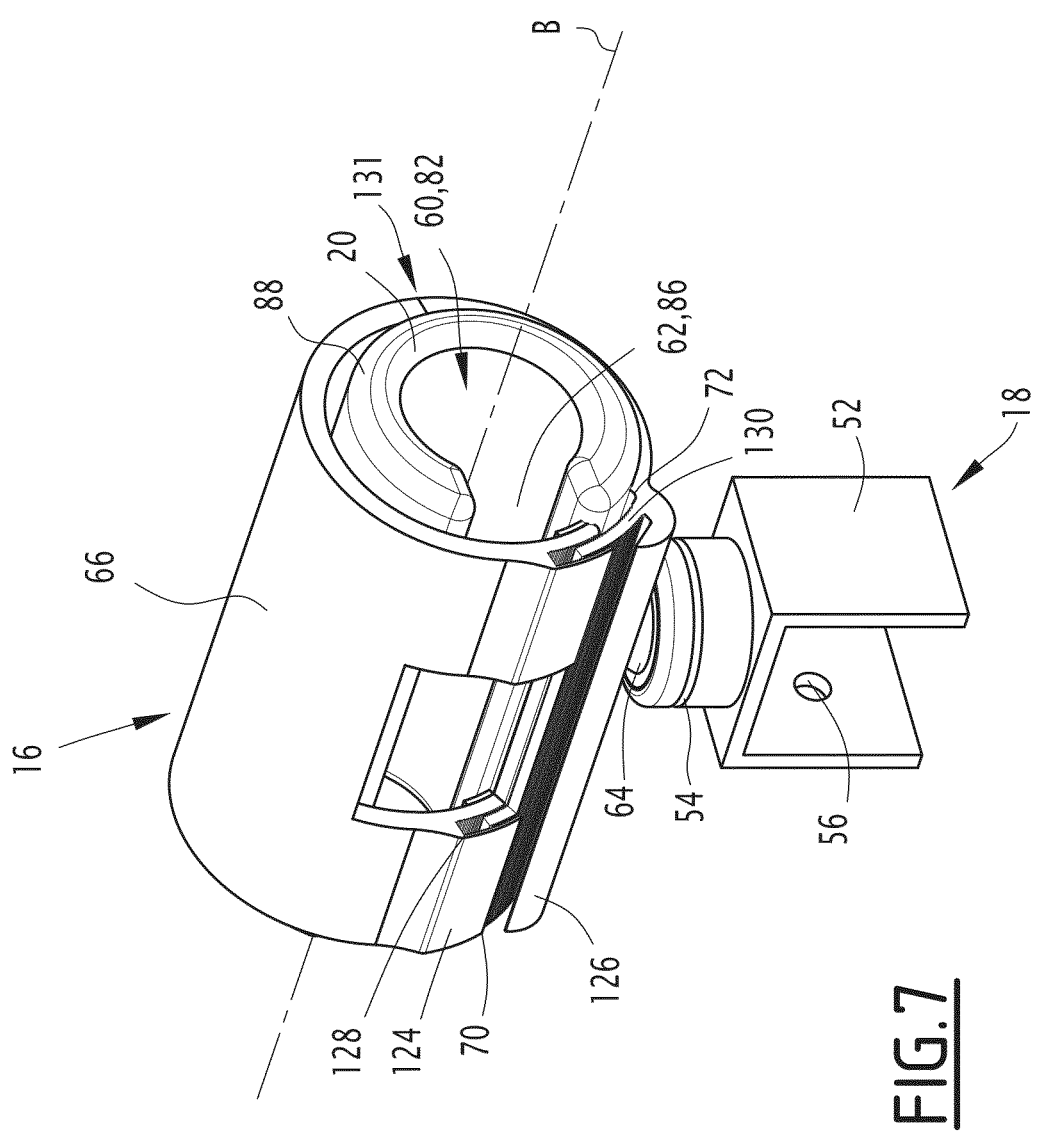
FIG. 7 is a perspective view of the receiving clip, the connecting assembly and a holding system of a fourth anchoring device according to the invention.

In one embodiment shown in FIG. 7, the clamping mechanism 68 of the sleeve 66 does not include the jaws 74, 76 but defines a notch system comprising a first portion 124 and a second portion 126.

The first portion 124 of the clamping mechanism 68 extends over the first edge 70 of the sleeve 66 and defines a notch 128 presenting internal teeth therein.

The second portion 126 of the clamping mechanism 68 extends over the second edge 72 of the sleeve 66 and defines a tab 130 presenting external teeth. The tab 130 extends facing the notch 128 of the first portion 124 and is intended to be inserted into the notch 128.

The insertion of the tab 130 into the notch 128 by pressing the first portion 124 toward the second portion 126 of the clamping mechanism 68 causes the first edge 70 to contact the second edge 72 of sleeve 66 and therefore causes the sleeve 66 to move into a closed position. The outer teeth on the tab 130 engage the inner teeth of the notch 128 to provide a lock in position.

The sleeve 66 comprises a hinge 131 extending according to a direction parallel to the longitudinal axis of the sleeve 66. Advantageously, the hinge 131 extends diametrically opposite the longitudinal opening 62.

Figure 10:
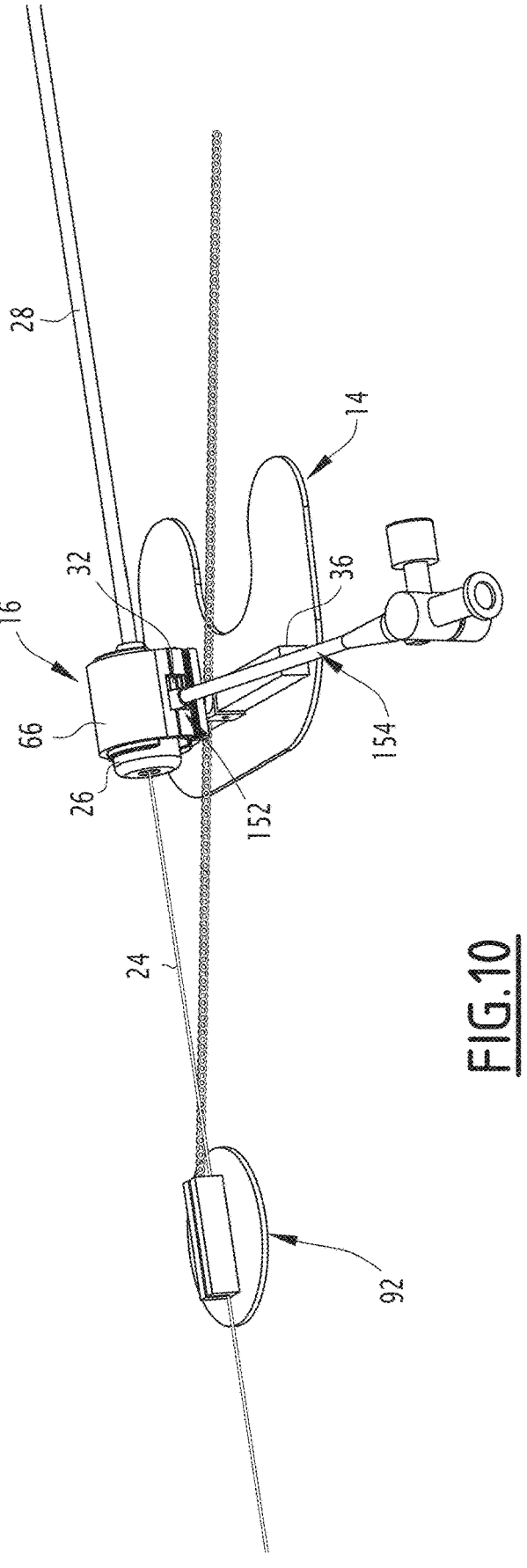
FIG. 10 is a perspective view of an alternative fourth anchoring device of FIG. 7.

In an alternative of this embodiment shown in FIG. 10, the receiving clip 16 is able to receive the hollow tip 26 of the introducer 12.

Advantageously, the sleeve 66 presents a notch 152 suitable for allowing passage of a pipe 154 introducing fluid connected to the sealing valve 32 located inside the tubular body 30 of the hollow tip 26.

According to another embodiment illustrated in FIG. 8, the clamping mechanism 68 of the sleeve 66 defines a toggle system comprising a first portion 132 and a second portion 134.

The first portion 132 defines a toggle and comprises an articulated lever 136 mounted in rotation parallel to the axis B on the first edge 70 of the sleeve 66 and a connecting rod 138 articulated to the lever 136 about an axis parallel to the axis B. The connecting rod 138 includes at its end a closing link 140 in the form of a crosspiece extending parallel to the axis B.

The second portion 134 is fixedly mounted on the second edge 72 of the sleeve 66 and defines a hook 144 capable of receiving the closing link 140.

The first portion 132 defines a first free position where it extends loosely on the first edge 70 of the sleeve 66, a second engaged position with the second portion, shown in FIG. 8 where the closing link 140 is locked in the hook 144 and the lever 136 is in the upper position, and a third position where the closing link 140 is locked in the hook 144 and the lever 136 is in the lower position.

Moving from the second position to the third position of the first portion 132 by pressing the lever 136 forces the connecting rod 138 to move to the lower position. The connecting rod 138 drives with it the second edge 72 of the sleeve 66 toward the first edge 70 and therefore the passage of the sleeve 66 to the closed position.

Moving from the third position to the second position of the first portion 132 by lifting the lever 136 returns the sleeve 66 to the open position to adjust the position of the introducer 12 during the surgical procedure.

Figure 9:
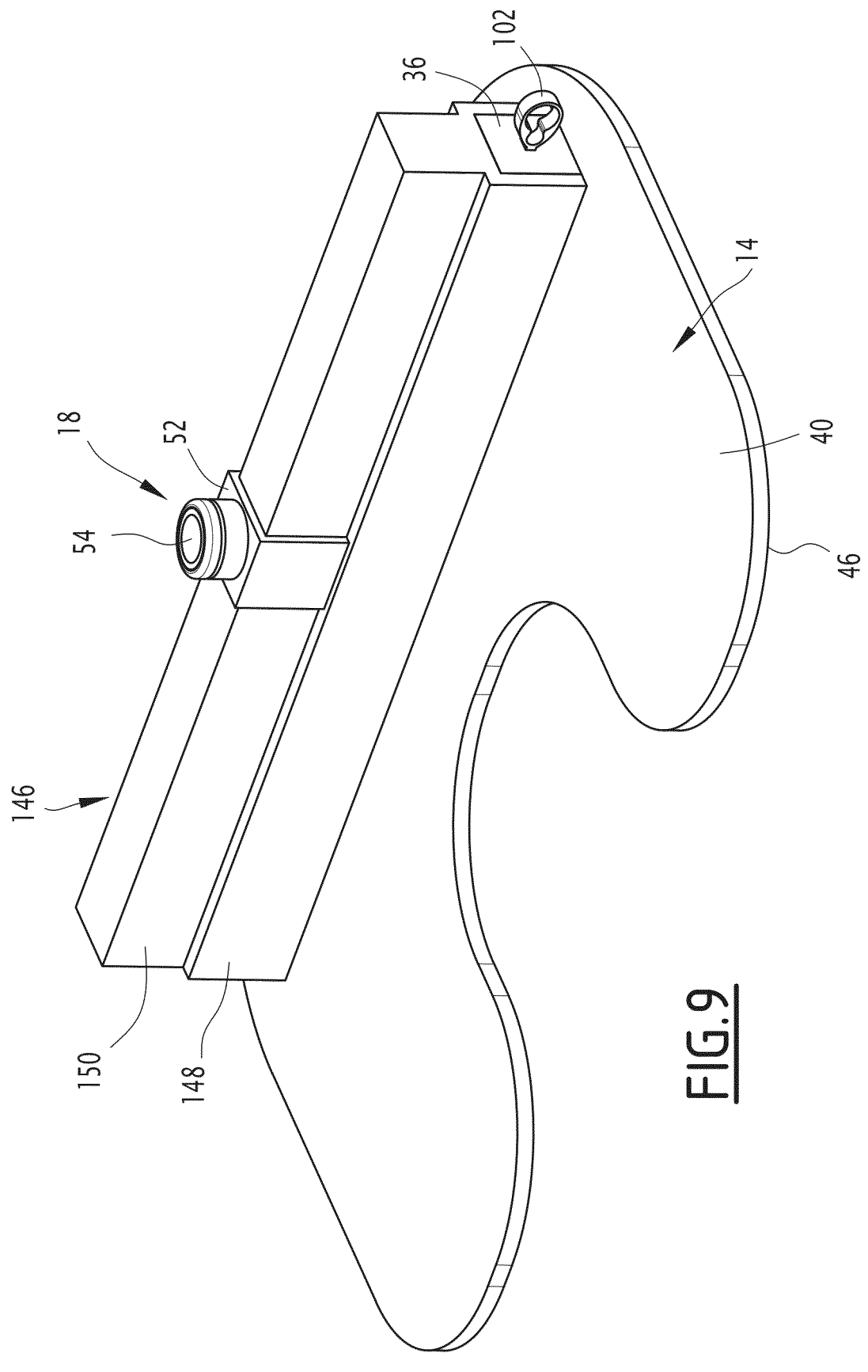
FIG. 9 is a perspective view of an alternative intermediate part comprised between the connecting assembly and the support of the anchoring device.

In one alternative shown in FIG. 9, the support 14 comprises at least one additional piece 146 that attaches to the bar 36 so as to increase the height of the support 14.

The additional piece 146 or stack of pieces 146 increases the height of the support 14 and thereby positions the introducer 12 at a desired height to, for example, maintain the angle of the introducer at the exit of the incision.

The part 146 comprises a first portion 148 defining a hollow cavity intended to receive the bar 36 and a second portion 150 of identical size to the bar 36 and intended to receive the connecting assembly 18.

The part 146 is mounted on the bar 36 by clipping the first portion 148 of the part 146 to the bar 36. The connecting assembly 18 is mounted to the second portion 180 of the part 146.

A first part 146 may be stacked on a second part 146 by clipping the first portion 148 of the first part 146 to the second portion 150 of the second part 146. This operation can be performed as many times as necessary to obtain a stack of parts 146 with the desired height.

The stack of parts 146 is secured to the bar 36 by clipping the first portion 148 of the part 146 located at the bottom of the stack on the bar 36 and the connecting assembly 18 is mounted to the second portion 150 of the part 146 located at the top of the stack.

Alternatively, another elevation system is used instead of the stack of parts 146, such as a screw system.

Figure 11:
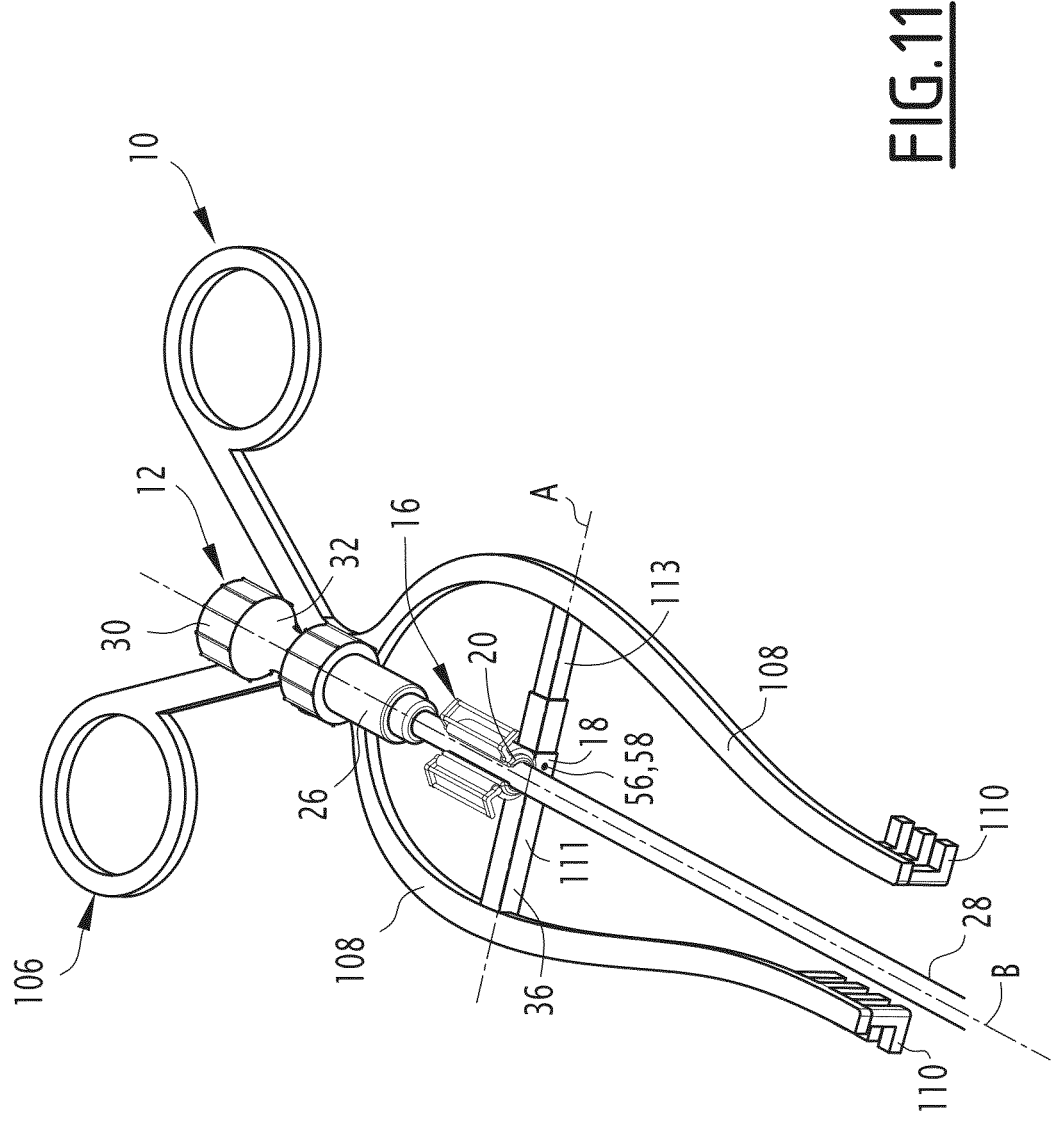
FIGS. 11 to 16 are perspective views of anchoring devices according to other embodiments of the invention.

In the alternative of the invention shown in FIG. 11, the support 14 includes a single-use retractor 106 with a bar 36 already mounted between the two legs 108 of the retractor 106. Such a single-use retractor 106 is, for example, made of a plastic material.

Figure 12:
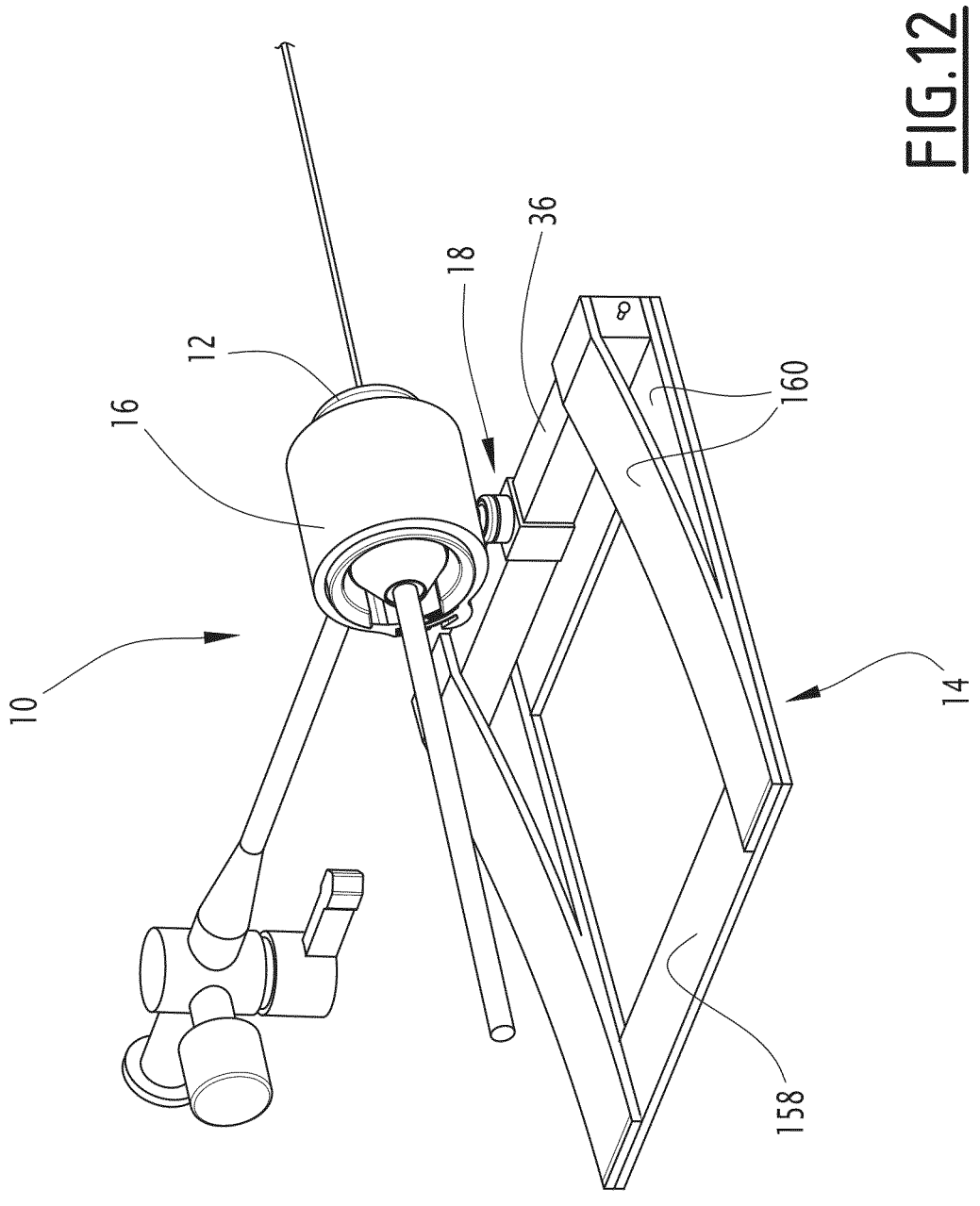

In the embodiment of the invention shown in FIG. 12, the support 14 includes a sterile field consisting of an adhesive film 158 defining a sterile barrier between its lower surface stuck to the skin of the patient and its surface. The adhesive film 158 has a central window therethrough.

In this embodiment, each end of the bar 36 is mounted between two metal retaining tabs 160 that are attached to the adhesive film 158.

Figure 13:
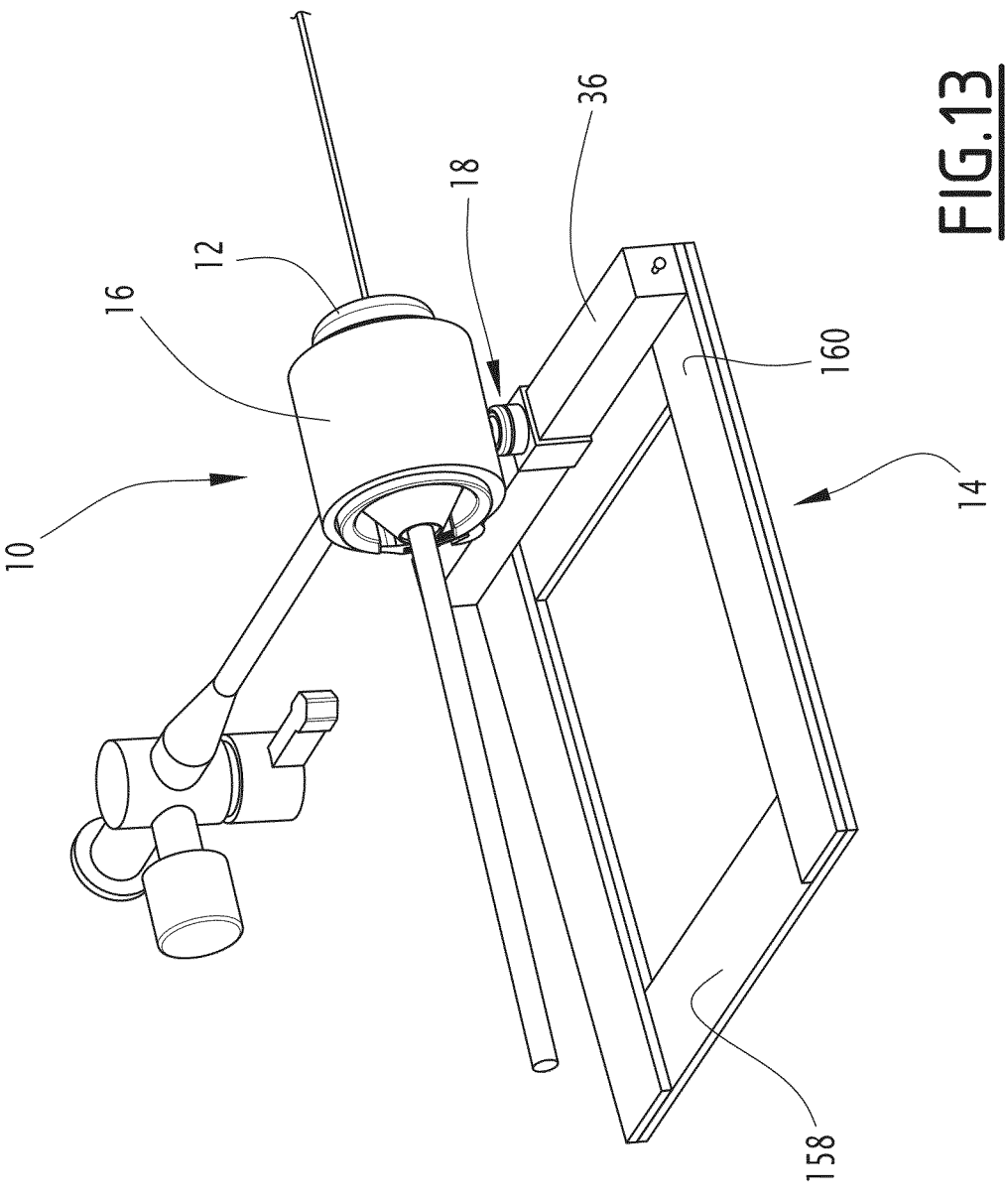

In the alternative embodiment shown in FIG. 13, each end of the bar 36 is mounted to a single metal holding tab 160 that is attached to the adhesive film 158.

Figure 14:
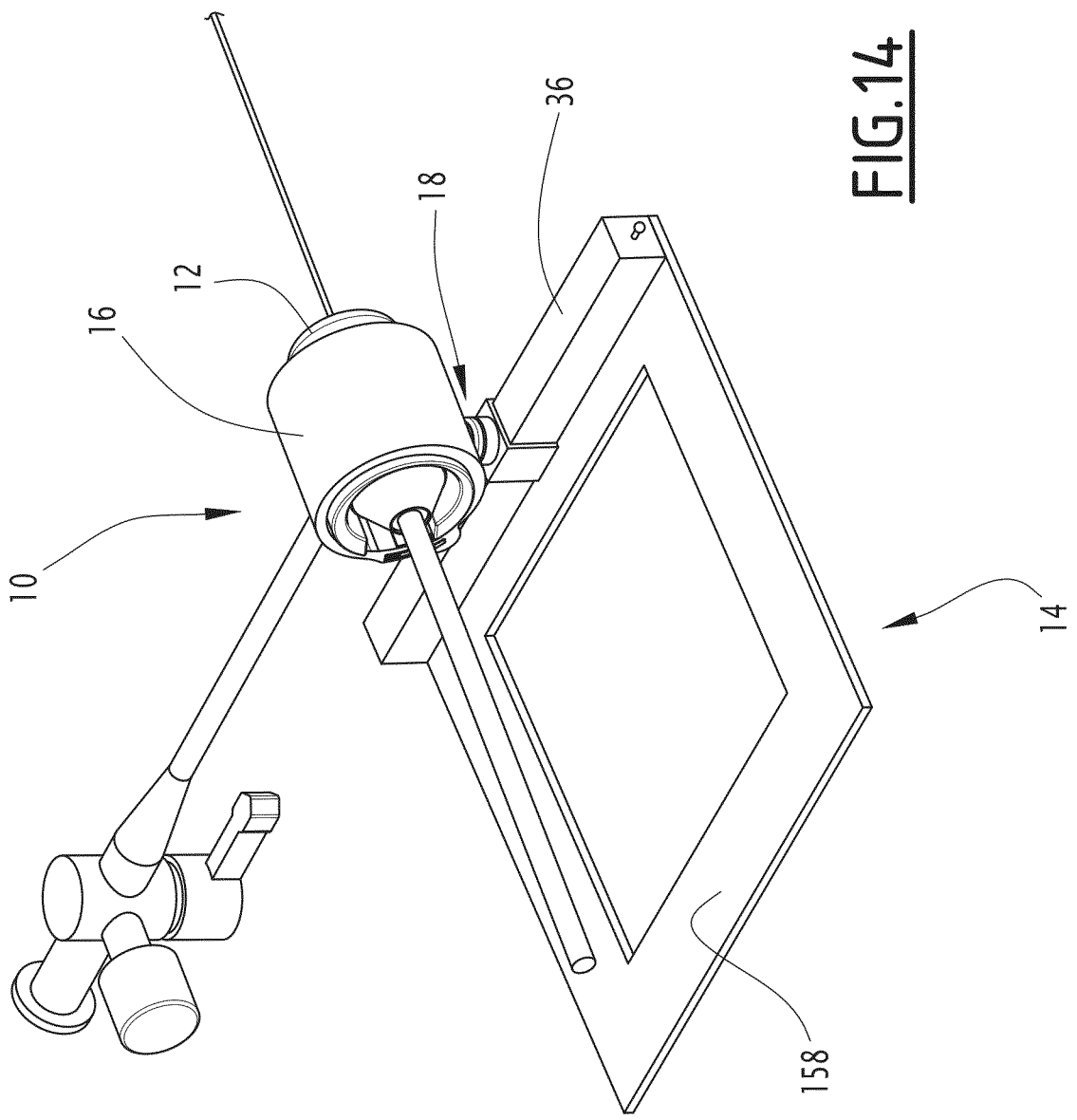

In the alternative illustrated in FIG. 14, the bar 36 is bonded directly to the adhesive film of the sterile field.

Figure 15:
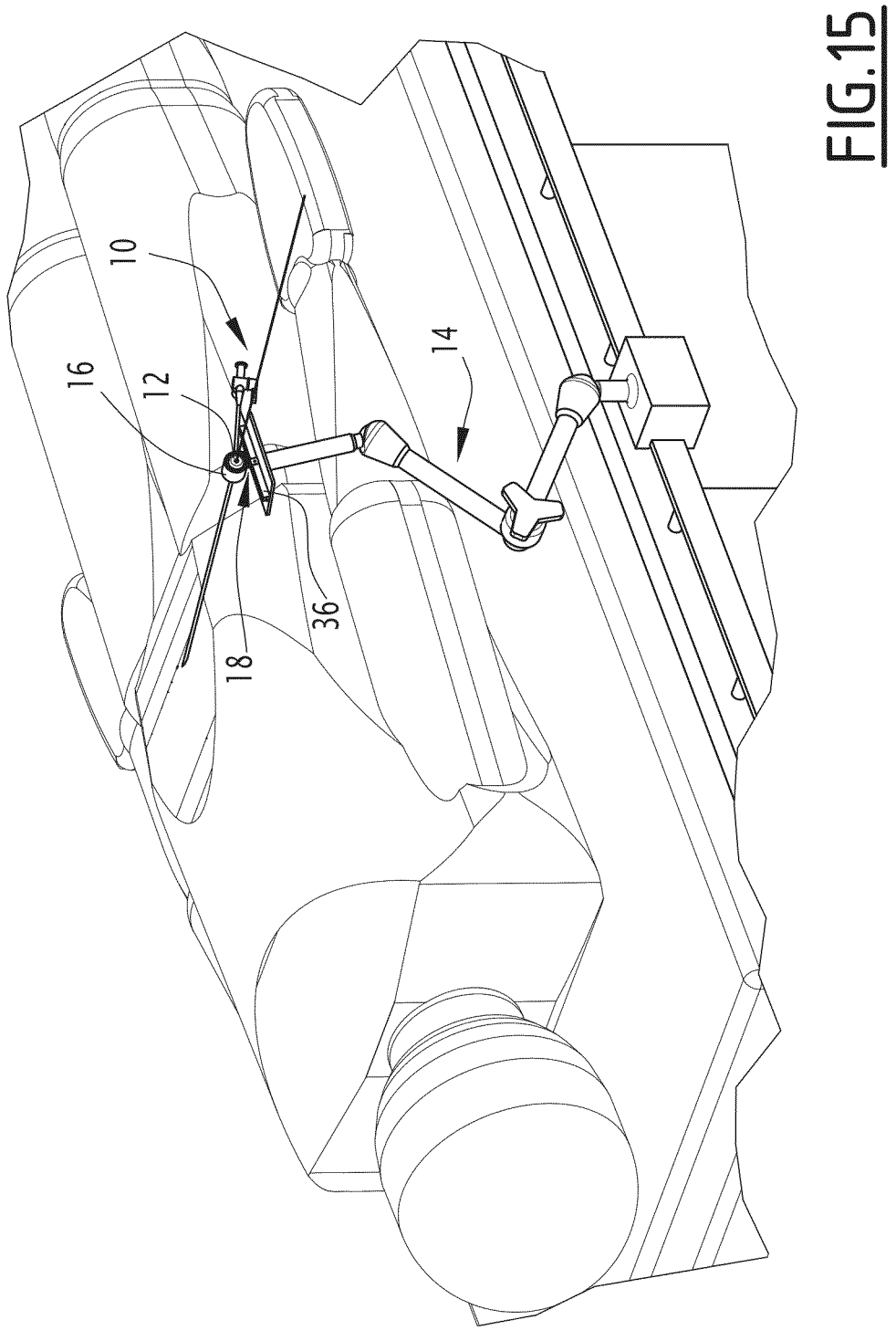
Figure 16:
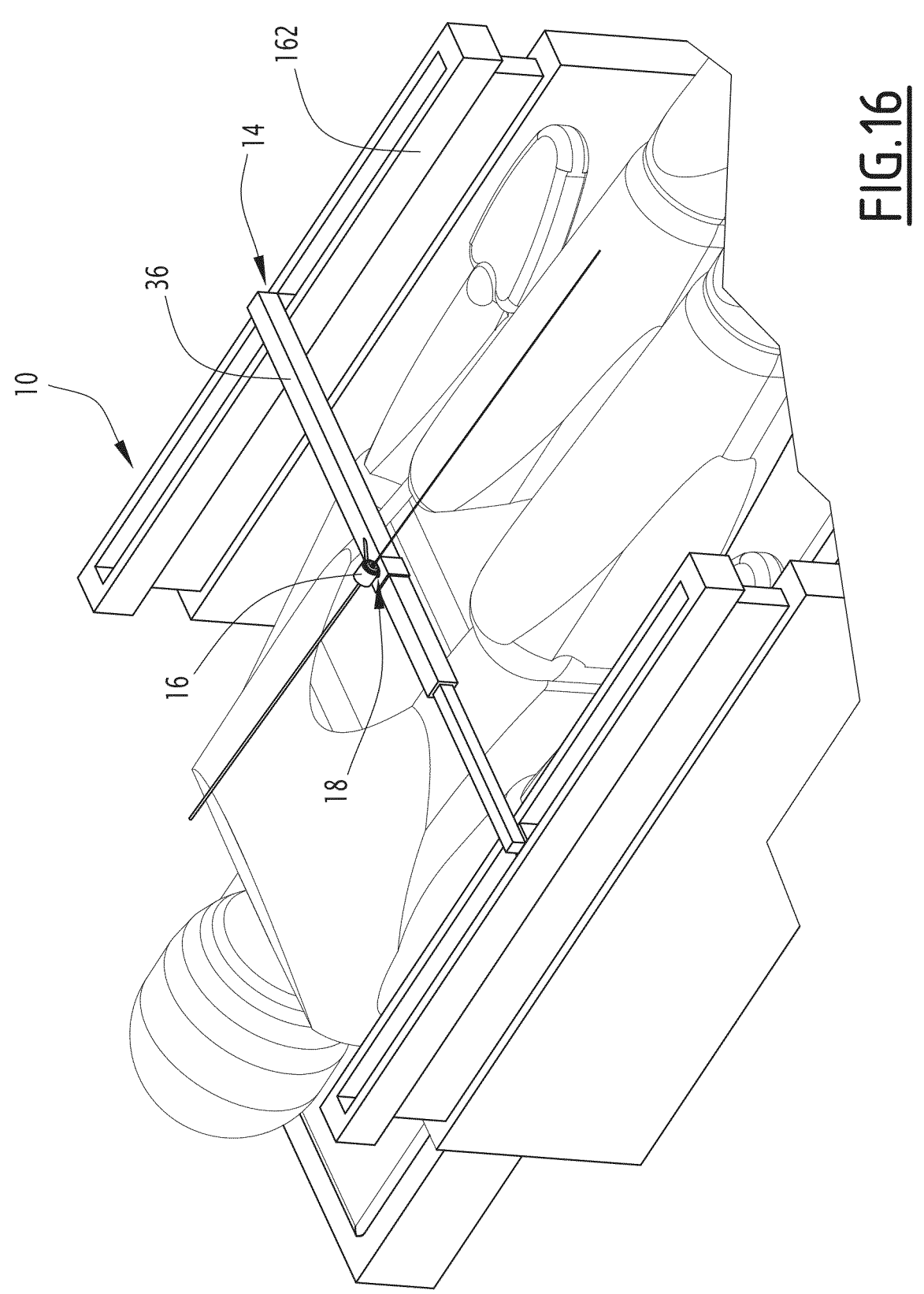

In an alternative of the invention illustrated in FIGS. 15 and 16, the support 14 is not held directly to the patient, but is held in a fixed manner relative to the patient.

By "held in a fixed manner relative to the patient" is meant, in particular, that the patient is immobilized on a surface, for example, of an operating table, with the support 16 held fixedly relative to the table and hence, relative to patient.

In the embodiment shown in FIG. 15, the support 14 includes an articulated arm attached at one end to the operating table on which the patient is lying. The bar 36 is attached to the other end of the articulated arm and is able to be positioned and held by means of the articulated arm in a desired position relative to the patient. The articulated arm is preferably radiotransparent.

In the embodiment shown in FIG. 16, the support 14 includes a rigid shell comprising two movable side walls 162. The rigid shell comprising the side walls 162 is preferably radiotransparent.

The patient is received on the rigid shell between the two side walls 162, which are moved toward the patient to abut against the patient on either side of the patient. The bar 36 extends between the two side walls 162 and forms a belt over the patient. The bar 36 is for example slidably mounted on rails defined on each of the side walls 162. Optionally, the bar 36 is also attached at each end thereof by an adhesive patch to the skin of the patient.

In one alternative of the invention, the anchoring device 10 comprises a plurality of guide fixing systems 22. Each of the guide fixing systems 22 is adapted to secure one type and/or diameter of surgical guide 24. The guide fixing systems 22 differ from one another in color and/or texture, so that they are easily differentiated and identified.

What is claimed is:

1. A device for anchoring an introducer of a medical device in a human body, the anchoring device comprising:
   a support configured to be held on a patient or relative to the patient;
   a connecting assembly mounted on the support;
   a receiving clip for the introducer attached to the connecting assembly to be mounted on the support, the receiving clip defining a central passage extending along a longitudinal axis and a longitudinal opening for insertion of the introducer into the central passage; and
   a holding system configured to hold the introducer in a position in the receiving clip,
   wherein the holding system includes at least one reversible locking pad for the introducer, the holding system being configured to change from a released configuration for positioning, displacing, or removing the introducer in the central passage to a configuration for locking the introducer in a position in the central passage,
   wherein the support includes a bar, the receiving clip being mounted on the bar of the support by the connecting assembly, and
   wherein the receiving clip is slidably mounted along the bar of the support.

2. The anchoring device according to claim 1, wherein the at least one reversible locking pad includes a sleeve split along a generatrix.

3. The anchoring device according to claim 1, wherein the at least one reversible locking pad is formed of a block of deformable material, or a bag containing deformable material.

4. The anchoring device according to claim 1, wherein the holding system comprises an inflation system for the at least one reversible locking pad controlling inflation and deflation of the at least one reversible locking pad.

5. The anchoring device according to claim 1, wherein the connecting assembly between the receiving clip and the support includes a ball and a ball joint receiving the ball.

6. The anchoring device according to claim 1, wherein the bar is configured to be extendable and a length of the bar is adjustable.

7. The anchoring device according to claim 1, wherein the support includes at least one additional piece attached to the bar to increase a height of the support.

8. The anchoring device according to claim 1, wherein the support includes a spacer.

9. The anchoring device according to claim 1, wherein the support includes a patch.

10. The anchoring device according to claim 1, wherein the receiving clip includes a sleeve deformable between an open position and a closed position.

11. The anchoring device according to claim 10, wherein the receiving clip includes a mechanism for clamping and/or unclamping the deformable sleeve.

12. The anchoring device according to claim 11, wherein the mechanism for clamping and/or unclamping the deformable sleeve comprises a notch system, a toggle system or a clamp system.

13. The anchoring device according to claim 1, comprising a guide fixing system remote from the receiving clip and the support.

14. The anchoring device according to claim 13, wherein the guide fixing system comprises a holding block attached to a patch defining a slot for receiving a guide.

15. The anchoring device according to claim 13, comprising a flexible link connecting the guide fixing system to the support or to the receiving clip.

16. The anchoring device according to claim 1, wherein the support includes a sterile field, an articulated arm, or a rigid shell.

17. A method for anchoring an introducer of a medical device, implemented outside a human body, the method comprising:
   providing a anchoring device including a support previously fixed to a patient or relative to the patient and a clip for receiving the introducer mounted on the support, the clip defining a central passage extending along a longitudinal axis and a longitudinal opening for inserting the introducer into the central passage, the anchoring device including a holding system configured to hold the introducer in a position in the clip, the holding system including at least one reversible locking pad for the introducer, the support including a bar, the clip being mounted on the bar of the support by a connecting assembly, the clip being slidably mounted along the bar of the support;
   positioning the introducer in the central passage through the longitudinal opening; and
   reversibly moving the at least one reversible locking pad from a released configuration upon placement of the introducer in the central passage to a configuration locking the introducer in a position in the central passage.

* * * * *